United States Patent [19]

Hines et al.

[11] 4,215,579

[45] Aug. 5, 1980

[54] COAL SAMPLING

[75] Inventors: David M. Hines, Crane Township, Wyondot County; Charles D. Waring, Marion Township, Marion County, both of Ohio

[73] Assignee: The Fairfield Engineering Company, Marion, Ohio

[21] Appl. No.: 22,303

[22] Filed: Mar. 20, 1979

[51] Int. Cl.² ............................................. G01N 1/20
[52] U.S. Cl. ........................................................ 73/424
[58] Field of Search ................ 73/421 R, 423 R, 424

[56] References Cited

U.S. PATENT DOCUMENTS

| 949,284 | 2/1910 | McCone | 73/421 R |
| 1,105,712 | 8/1914 | Sturtevant | 73/421 R |
| 1,238,058 | 8/1917 | Backus | 73/424 |
| 3,683,702 | 8/1972 | O'Brien | 73/423 |

FOREIGN PATENT DOCUMENTS 425930  3/1935  United Kingdom ..................... 73/424

*Primary Examiner*—S. Clement Swisher
*Attorney, Agent, or Firm*—Buell, Blenko & Ziesenheim

[57] ABSTRACT

The specification discloses portable coal sampling apparatus including an enclosure, a primary sample receiving hopper, a primary sample crusher arranged to receive coal from the hopper and deliver crushed coal to the enclosure, and a secondary sample collector within the enclosure.

4 Claims, 6 Drawing Figures

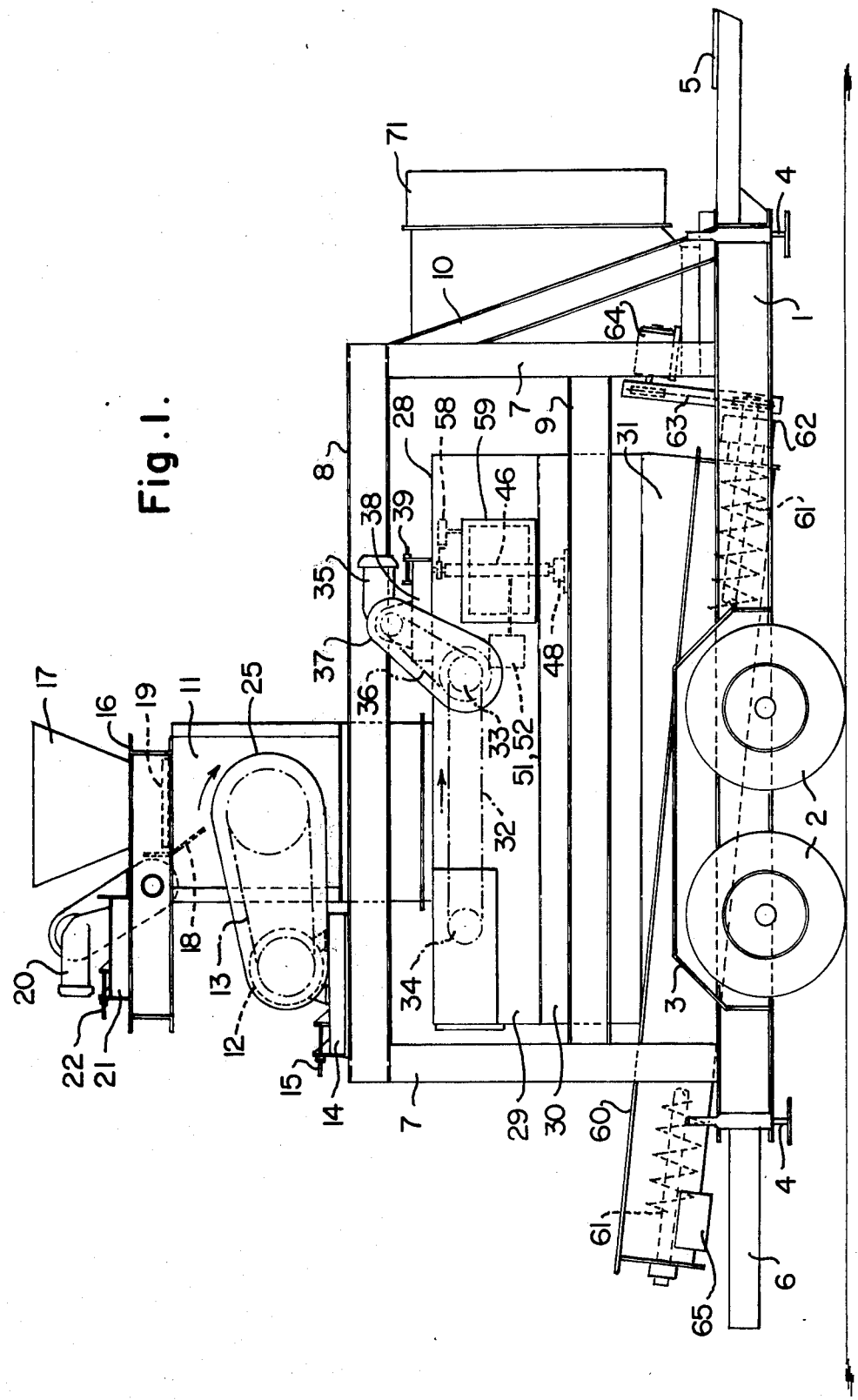

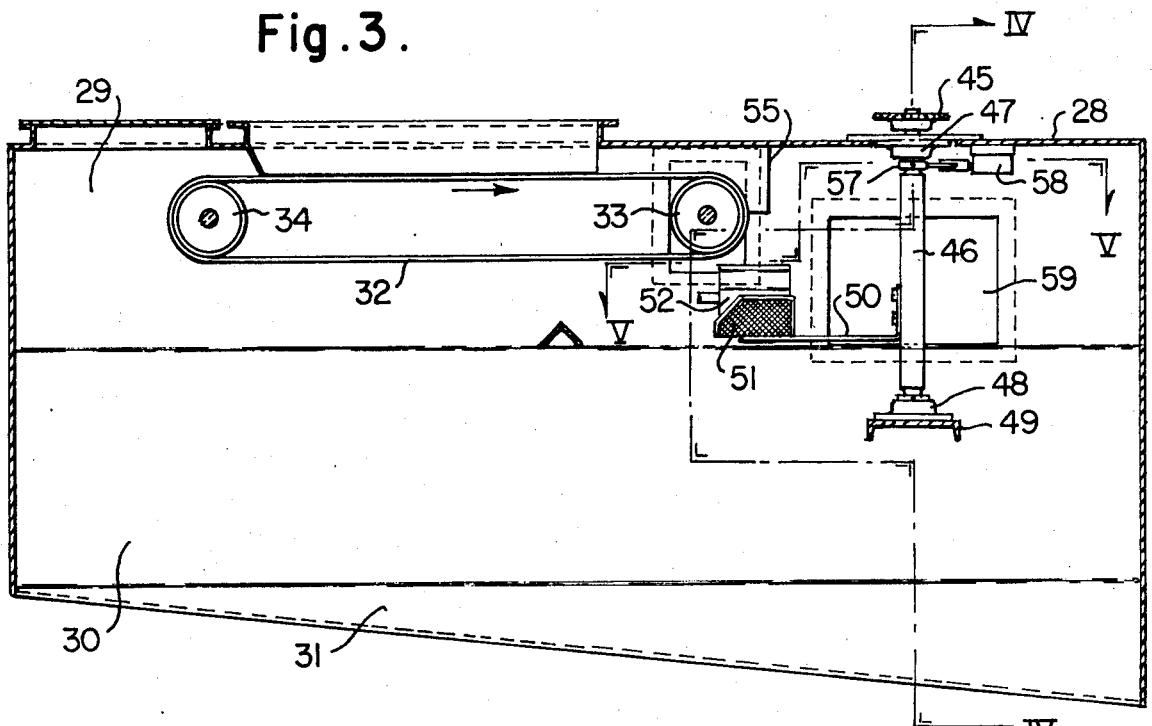
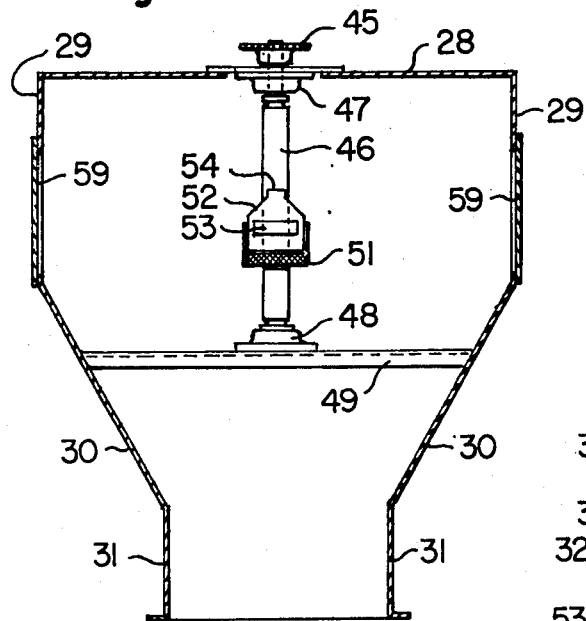
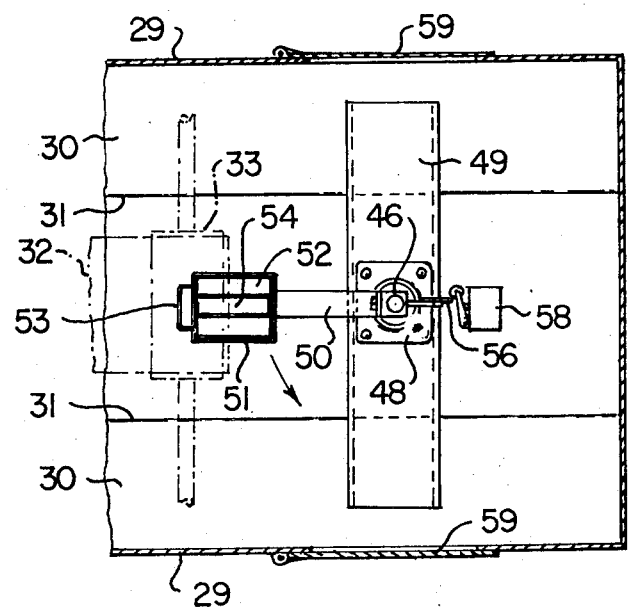

COAL SAMPLING

This invention relates to taking samples of coal. More particularly it relates to a mobile sampler which may readily be moved to a location for as long as needed and thereafter to a different location as a self contained unit.

The use of coal sampling apparatus is well-known and is common wherever large quantities of coal are used for fuel or as a raw material, as in a power plant or coke ovens. In most such installations sampling equipment is installed in the plant to sample feed from the storage yard as the coal reaches the plant. It may be desirable, however, to take samples in the field or at the time of delivery. For those conditions a mobile sampler of some type is required.

Our invention permits a primary sample to be taken directly at the site from a transporting vehicle or a stock pile. We crush the primary sample and reduce it in volume to a secondary sample which is also taken at the site while the remainder of the primary sample is returned to stock. The volume of material which must be taken to the laboratory is very significantly less than is the case when a primary non-reduced sample is taken to the laboratory. Crushing of the primary sample at the field site reduces the amount of laboratory dirt and makes possible more convenient handling and analysis of a secondary sample.

We provide a mobile sampler having primary sample receiving means, primary sample crushing means and secondary sample taking means. We prefer to provide a primary sample and crush the same after which the crushed material is discharged in a stream from which a secondary sample is cut on a periodic basis. We prefer to process the primary sample and to take the secondary sample in a protected zone where effects of wind and ambient atmospheric conditions are reduced. We prefer to provide an enclosed zone within which the primary sample is processed and the secondary sample taken. The likelihood of the primary sample being contaminated by handling or exposure before reaching the laboratory is thereby reduced to a minimum. We further provide means for returning that portion of the primary sample which is not taken as secondary sample directly to the source without further handling. We prefer to provide access openings to the enclosed zone and provide control means whereby the second sample is automatically positioned adjacent an access opening for ready removal of the sample from the sampling apparatus.

Other details, objects and advantages of our invention will become more apparent as the following description of a present preferred embodiment thereof proceeds.

In the accompanying drawings we have illustrated a present preferred embodiment of our invention in which FIG. 1 is a side elevational view of sampling apparatus incorporating our invention;

FIG. 3 is an enlarged sectional view of part of the apparatus illustrated in FIG. 1 showing the crushed coal conveyer belt and sample cutter;

FIG. 4 is a sectional view taken on line IV—IV of FIG. 3;

FIG. 5 is a plan view of the apparatus shown in FIG. 4; and

Figure 6:
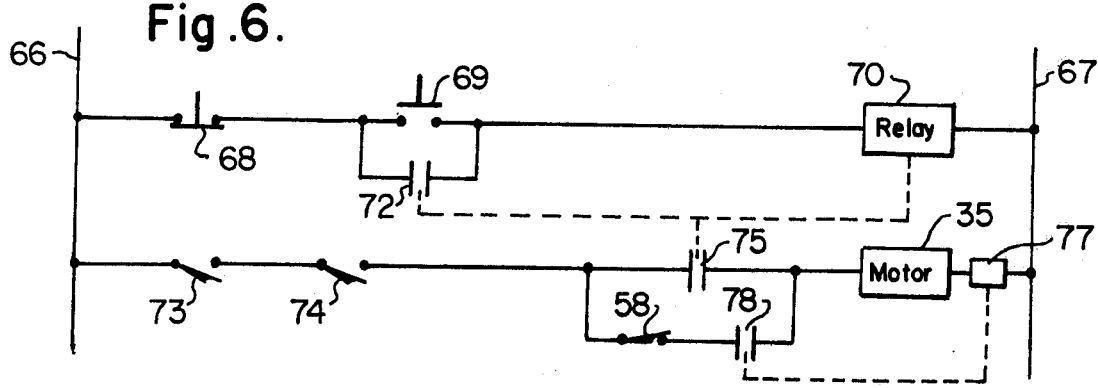
FIG. 6 is a schematic wiring diagram showing the motor circuit for the crushed coal conveyor belt and sample cutter.
Figure 2:
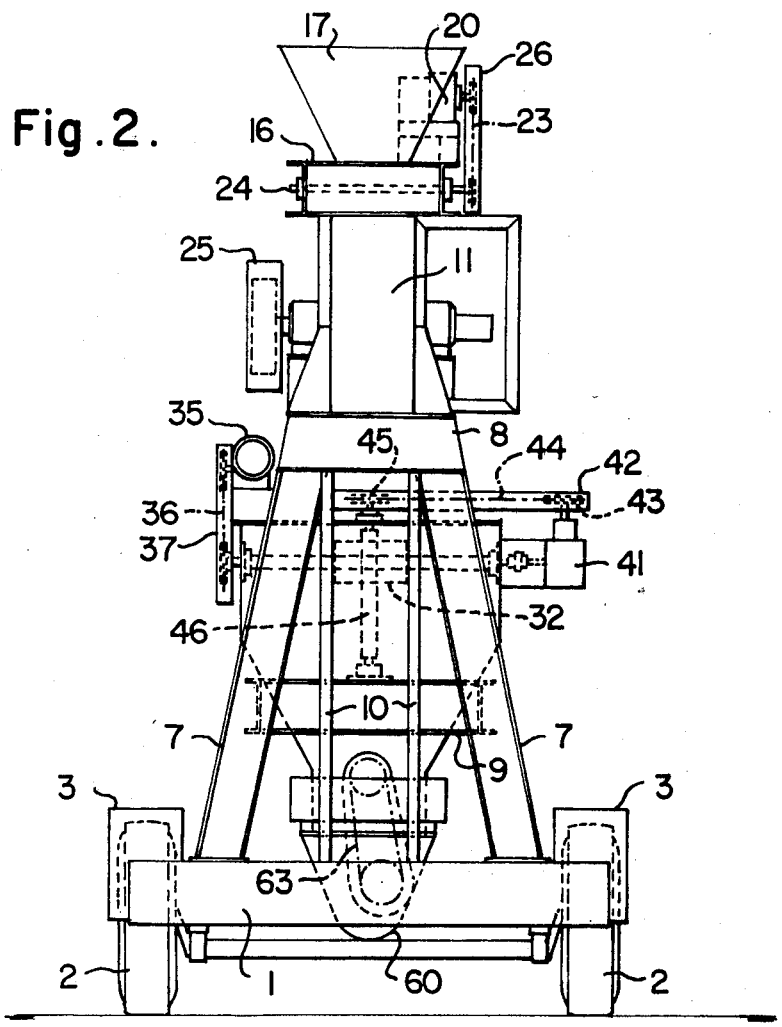
FIG. 2 is an end elevational view of the apparatus shown in FIG. 1 with the control panel removed for clarity of illustration.

The sampler is mounted upon a vehicle chassis comprising a rectangular frame 1 mounted on rubber tired wheels 2 in a conventional manner. Mud guards 3 are fitted above wheels 2. Jacks 4 are fitted at the corners of frame 1 to permit the frame to be leveled and held securely in position at the job site. A tongue 5 is provided at one end for towing and a projecting bumper or guard 6 is provided at the opposite end to protect the mechanism while being towed on the highway or at the job site.

An upwardly extending frame is mounted upon the chassis. The frame comprises inwardly sloping columns 7 at each end of the chassis. An upper frame 8 is mounted on the tops of columns 7 extending from end to end of the sampler. An intermediate frame 9 is mounted to columns 7 below upper frame 8 and above chassis frame 1. The structure comprising columns 7, upper frame 8 and intermediate frame 9 is braced by sloping buttress members 10 which connect between one end of chassis frame 1 and the upper end of columns 7 and upper frame 8 adjacent the same end.

A crusher 11 is mounted on upper frame 8. Crusher 11 is of conventional design and serves to crush coal to a small size consist suitable for sampling. Crusher 11 is driven by a motor 12 through drive belt 13. Motor 12 is mounted on a base 14, and a take-up screw 15 is provided to shift the motor to maintain desired tension of drive belt 13.

A hopper frame 16 is mounted on top of crusher 11. Hopper frame 16 carries a hopper 17 open at the top to receive coal. A deflector 18 directs the coal from hopper 17 into crusher 11 along a desired path. A movable gate 19 is provided in the bottom of hopper 17. Gate 19 is movable between an open position and a closed position. It is driven by a gear motor 20 mounted on base 21 and having a take-up screw 22. The drive for gate 19 is through drive belt 23 and shaft 24. Drive belts 13 and 23 are protected by belt guards 25 and 26, respectively.

A sampling enclosure 27 is mounted within the structure comprising columns 7, upper frame 8 and intermediate frame 9. Sampling enclosure 27 comprises a top panel 28, side panels 29 and inwardly tapering transition panels 30 below side panels 29. The transition section terminates in a downwardly extending trunk formed by panels 31.

A belt conveyor 32 is mounted on head shaft 33 and tail shaft 34 within sampling enclosure 27. The two shafts are carried by journals on side panels 29. Head shaft 33 is driven by a gear motor 35 through a drive belt 36 protected by a guard 37. Gear motor 35 is mounted on a base 38 having a belt take-up 39. Belt conveyor 32 is located beneath sampler 11 in position to receive crushed coal discharged from sampler 11.

Head shaft 33 is connected to input shaft 40 of gear box 41 having an output shaft 42 carrying a chain sprocket 43. An endless chain 44 extends around sprocket 43 and a sprocket 45 mounted on vertical shaft 46. Shaft 46 is mounted in a journal 47 on top panel 28 and a journal 48 on a cross member 49 mounted within sampling enclosure 27. An arm 50 extends horizontally from shaft 47 and carries a basket 51 formed from expanded metal mesh. A sample collector box 52 is fitted in basket 51. Box 52 has a handle 53 at one end and has a narrow open slot 54 at its upper end. When box 52 is placed in basket 51 and the rotational position of shaft 47 is such that arm 50 projects toward belt 32, box 52 will be beneath the end of belt 32 wrapping around head shaft 33 in a position to receive coal which is falling free from belt 32.

A skirt member 55 is fitted along each edge of belt 32 adjacent head shaft 33 and prevents a material on the belt from spilling over the side.

A trigger 56 extends radially from shaft 47. Trigger 56 is mounted on a collar 57 which is locked in position on shaft 47 by a set screw. Trigger 56 may be rotated relative to shaft 47 by loosening the set screw, moving the trigger through a desired angle and then tightening the set screw. Once on each revolution of shaft 47 trigger 56 will contact a switch 58 fitted to the under surface of top panel 28. Access doors 59 are fitted in side panels 29 opposite to shaft 47.

The bottom of panels 31 are joined to a conveyor housing 60 which extends from one end to the other of the sampler. Housing 60 carries a screw conveyor 61 driven through a gear box 62 by drive chain 63 and motor 64. Rotation of screw 61 carries material toward outlet 65 from which the material is discharged.

A simplified and schematic wiring diagram for control of motor 35 is shown in FIG. 6. The circuit includes power lines 66 and 67. A connection extends from line 56 through normally closed motor stop switch 68, normally open motor start switch 69, and relay 70 to line 67. Switches 68 and 69 as well as other controls for the sampler are mounted upon control panel 71. A bypass to motor start switch 69 is provided through switch 72 operated by relay 70. Switch 72 is normally open but is closed when relay 70 is energized. A second connection between lines 66 and 67 is made by switch 73, switch 74, switch 75, motor 76, and relay 77. Switch 75 is normally open but is closed when relay 70 is energized. A bypass to switch 25 is provided through switch 58 and switch 78. Switch 78 is normally open but is closed when relay 77 is energized.

Switches 73 and 74 are mounted on side panels 29 to sense the positions of access doors 59. If a door 59 is opened the associated switch will also open.

The sampler is used by first taking a gross sample from a larger quantity which is to be sampled. The material is placed in hopper 17 while gate 19 is closed. When sampling is to begin access doors 59 are closed and the motor start button is pressed to close the switch 69 momentarily. A circuit will then be completed through relay 70 causing switch 72 and switch 75 to be closed. The closing of switch 72 holds relay 70 energized after the motor start button is released and switch 69 opens. Relay 70 will also close switch 75 completing a circuit through circuits 73, 74 and 75, motor 35 and relay 77. Motor 35 will then drive belt 32 and cause shaft 47 to rotate. Energizing of relay 77 will close normally open switch 78 completing a bypass circuit around switch 75 through switches 58 and 78. Switch 58 will be momentarily opened by trigger 56 once on each revolution of shaft 47. So long as switch 75 remains closed, however, the momentary opening of switch 58 will not affect operation of motor 35.

When sampling is to begin motor 20 is energized to slowly open gate 19. The slow opening of the gate will permit a gradual discharge of coal from hopper 17 to prevent an accumulation and slugging within the crusher leading to non-uniform results between the beginning and end of the sample from hopper 17. Coal discharged from the hopper is crushed in crusher 11 and discharged in finely divided form onto belt 32. As shaft 47 revolves basket 51 and sample box 52 will periodically pass through material discharging off the end of conveyor belt 32 and will take a narrow cut from the stream through opening 54 in sample box 52. The sample box will take repeated cuts until the entire supply of coal in hopper 17 has been exhausted and has passed through crusher 11 and conveyer belt 32.

After hopper 17 has been emptied motor 20 may be reversed to close gate 19 and a new primary sample placed in hopper 17. After the crusher has cleared and the last coal has passed from belt 32, motor stop button 68 is pushed momentarily opening a switch 68. Relay 70 will thereby be deenergized. Motor 35 will continue to operate, however, on the circuit through switches 73, 74, 58 and 78 when trigger 56 momentarily opens switch 58 relay 77 will be deenergized causing switch 78 to open and motor 35 will come to a stop. By adjustment of collar 57 on shaft 47, motor 35 can be arranged to stop with basket 51 and sample box 52 opposite either access door which is desired. The access door is then opened, the sample box is removed and a substitute sample box inserted. Access door 59 is closed and motor 35 is restarted by pushing the motor start button to momentarily close switch 69. Motor 20 may then be energized to again open gate 19 and to crush and take a new sample in the same manner.

Coal which comes through crusher 11 and which is not taken in the sample box falls from conveyer belt 32 to the bottom of sample enclosure 27 and conveyor housing 60. When it is desired to remove coal from the bottom of sample enclosure 27, motor 64 is energized to drive screw conveyor 61 and convey the coal to outlet 65.

Sampling enclosure 27 protects the sample from affects of wind and moisture. Accordingly, the likelihood of distortion of the sample due to blowing of fines or inadvertent pick up of moisture is reduced as far as practicable.

While we have illustrated and described a present preferred embodiment of our invention it is to be understood that our invention is not limited thereto and may be otherwise variously practiced within the scope of the following claims.

We claim:

1. Sampling apparatus for coal and the like comprising a housing surrounding and enclosing a space, a primary sample crusher mounted adjacent the housing, a receiving hopper for coal and the like positioned to receive coal and the like outside the housing and to supply coal and the like to the primary crusher, a discharge from the primary crusher disposed to deliver crushed material within the housing, a conveyor belt within the housing, the conveyor being positioned below the primary crusher discharge to receive crushed material therefrom and to convey the crushed material to the end of the belt for free fall within the housing, a swingable arm located within the housing and positioned adjacent the end of the conveyor belt from which material is delivered, a sample container holder on the swingable arm, a sample container mounted in the holder, said arm and sample container being positioned for movement of the sample container across and through a stream of material falling from the end of the conveyor belt, drive means in driving relationship to both the conveyor belt and the swingable arm whereby the swingable arm is driven in fixed relation to the speed of the conveyor belt.

2. The coal sampling apparatus of claim 1 having conveyer means for removal of crushed coal from the bottom of the enclosure.

3. The coal sampling apparatus of claim 1 having a movable gate operable to controllably restrict flow of coal from the primary sample receiving hopper to the primary sample crusher.

4. Apparatus as set forth in claim 1 in which the enclosed space is provided with access door means and interlock means which stop sampling when the access door means are open.

* * * * *